US008435566B2

(12) United States Patent
Behnam et al.

(10) Patent No.: US 8,435,566 B2
(45) Date of Patent: *May 7, 2013

(54) DEMINERALIZED BONE MATRIX COMPOSITIONS AND METHODS

(75) Inventors: Keyvan Behnam, Red Bank, NJ (US); Guobao Wei, Milltown, NJ (US); James A. Beisser, Union Beach, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/526,987

(22) Filed: Jun. 19, 2012

(65) Prior Publication Data
US 2012/0258178 A1 Oct. 11, 2012

Related U.S. Application Data

(63) Continuation of application No. 12/254,619, filed on Oct. 20, 2008, now Pat. No. 8,202,539.

(60) Provisional application No. 60/981,395, filed on Oct. 19, 2007.

(51) Int. Cl.
A61K 9/10 (2006.01)
A61K 35/32 (2006.01)

(52) U.S. Cl.
USPC .......................................... 424/488; 424/549

(58) Field of Classification Search .................. 424/448, 424/549
See application file for complete search history.

(56) References Cited

U.S. PATENT DOCUMENTS

| | | |
|---|---|---|
| 4,172,128 A | 10/1979 | Thiele et al. |
| 4,294,753 A | 10/1981 | Urist |
| 4,394,370 A | 7/1983 | Jefferies |
| 4,430,760 A | 2/1984 | Smestad |
| 4,440,370 A | 4/1984 | Rood |
| 4,440,750 A | 4/1984 | Glowacki et al. |
| 4,455,256 A | 6/1984 | Urist |
| 4,472,840 A | 9/1984 | Jefferies |
| 4,485,097 A | 11/1984 | Bell |
| 4,563,350 A | 1/1986 | Nathan et al. |
| 4,619,989 A | 10/1986 | Urist |
| 4,657,548 A | 4/1987 | Nichols |
| 4,678,470 A | 7/1987 | Nashef et al. |
| 4,743,259 A | 5/1988 | Bolander et al. |
| 4,755,184 A | 7/1988 | Silverberg |
| 4,761,471 A | 8/1988 | Urist |
| 4,774,228 A | 9/1988 | Seyedin et al. |
| 4,774,322 A | 9/1988 | Seyedin et al. |
| 4,787,906 A | 11/1988 | Haris |
| 4,789,663 A | 12/1988 | Wallace et al. |
| 4,789,732 A | 12/1988 | Urist |
| 4,795,804 A | 1/1989 | Urist |
| 4,804,744 A | 2/1989 | Sen |
| 4,810,691 A | 3/1989 | Seyedin et al. |
| 4,843,063 A | 6/1989 | Seyedin et al. |
| 4,902,296 A | 2/1990 | Bolander et al. |
| 5,041,138 A | 8/1991 | Vacanti et al. |
| 5,073,373 A | 12/1991 | O'Leary |
| 5,106,748 A | 4/1992 | Wozney et al. |
| 5,166,187 A | 11/1992 | Collombel et al. |
| 5,211,664 A | 5/1993 | Tepic et al. |
| 5,236,456 A | 8/1993 | O'Leary et al. |
| 5,266,683 A | 11/1993 | Oppermann et al. |
| 5,270,300 A | 12/1993 | Hunziker |
| 5,284,655 A | 2/1994 | Bogdansky et al. |
| 5,290,558 A | 3/1994 | O'Leary et al. |
| 5,290,763 A | 3/1994 | Poser et al. |
| 5,314,476 A | 5/1994 | Prewett et al. |
| 5,336,264 A | 8/1994 | Constanz et al. |
| 5,354,557 A | 10/1994 | Oppermann et al. |
| 5,378,469 A | 1/1995 | Kemp et al. |
| 5,385,887 A | 1/1995 | Yim et al. |
| 5,405,390 A | 4/1995 | O'Leary et al. |
| 5,490,962 A | 2/1996 | Cima et al. |
| 5,501,706 A | 3/1996 | Arenberg |
| 5,507,813 A | 4/1996 | Dowd et al. |
| 5,518,680 A | 5/1996 | Cima et al. |
| 5,531,735 A | 7/1996 | Thompson |
| 5,563,124 A | 10/1996 | Damien et al. |
| 5,571,189 A | 11/1996 | Kuslich |
| 5,607,269 A | 3/1997 | Dowd et al. |
| 5,618,339 A | 4/1997 | Ito |

(Continued)

FOREIGN PATENT DOCUMENTS

| | | |
|---|---|---|
| DE | 2 253 086 | 9/1974 |
| DE | 693 24117 T2 | 6/1994 |

(Continued)

OTHER PUBLICATIONS

Aspenberg et al., "Monkey Bone Matrix Induces Bone Formation in the Athymic Rat, but Not in Adult Monkeys," J. of Orthop. Res. 9:20-25 (1991).

Aspenberg P. et al., "Bone morphogenetic protein induces bone in the squirrel monkey, but bone matrix does not", Acta Orthop Scand. 63(6):619-22 (Dec. 1992).

Blumenthal et al. "The use of collagen membrane barriers in conjunction with combined demineralized bone-collagen gel implants in human infrabony defects," J. Periodontal 61(6): 319-32 (Jun. 1990).

(Continued)

Primary Examiner — Marcia S Noble
(74) Attorney, Agent, or Firm — Sorell, Lenna and Schmidt LLP

(57) ABSTRACT

Bone matrix compositions and, more specifically, demineralized bone matrix (DBM) having increased osteoinductive capacity and methods for its production are provided. Specifically, DBM derived from cortical bone from the periosteal layer of bone are provided. Compositions comprising a disproportionate amount of DBM prepared from bone derived from the periosteal and/or middle layer of bone are provided. Preparations of and methods of use of periosteal DBM compositions are disclosed.

18 Claims, 6 Drawing Sheets

U.S. PATENT DOCUMENTS

| | | | |
|---|---|---|---|
| 5,658,882 A | 8/1997 | Celeste et al. |
| 5,723,012 A | 3/1998 | Fages et al. |
| 5,725,579 A | 3/1998 | Fages et al. |
| 5,776,193 A | 7/1998 | Kwan et al. |
| 5,788,959 A | 8/1998 | Singh |
| 5,807,437 A | 9/1998 | Sachs et al. |
| 5,830,493 A | 11/1998 | Yokota et al. |
| 5,846,484 A | 12/1998 | Scarborough et al. |
| 5,877,005 A | 3/1999 | Castor et al. |
| 5,894,070 A | 4/1999 | Hansson et al. |
| 5,899,939 A | 5/1999 | Boyce et al. |
| 5,902,562 A | 5/1999 | Lagasse et al. |
| 5,912,131 A | 6/1999 | Eyre |
| 6,007,580 A | 12/1999 | Lehto et al. |
| 6,018,095 A | 1/2000 | Lerch et al. |
| 6,030,635 A | 2/2000 | Gertzman et al. |
| 6,117,646 A | 9/2000 | Qvist et al. |
| 6,120,558 A | 9/2000 | Poddevin et al. |
| 6,124,273 A | 9/2000 | Drohan et al. |
| 6,143,030 A | 11/2000 | Schroder |
| 6,149,864 A | 11/2000 | Dillow et al. |
| 6,162,258 A | 12/2000 | Scarborough et al. |
| 6,180,606 B1 | 1/2001 | Chen et al. |
| 6,197,325 B1 | 3/2001 | MacPhee et al. |
| 6,217,614 B1 | 4/2001 | Fages et al. |
| 6,245,537 B1 | 6/2001 | Williams et al. |
| 6,294,041 B1 | 9/2001 | Boyce et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,352,667 B1 | 3/2002 | English |
| 6,372,257 B1 | 4/2002 | Marchosky |
| 6,387,391 B1 | 5/2002 | Shikinami et al. |
| 6,436,138 B1 | 8/2002 | Dowd et al. |
| 6,440,444 B2 | 8/2002 | Boyce et al. |
| 6,465,168 B1 | 10/2002 | Castor et al. |
| 6,468,543 B1 | 10/2002 | Gilbertson et al. |
| 6,478,825 B1 | 11/2002 | Winterbottom et al. |
| 6,592,886 B1 | 7/2003 | Zimmermann |
| 6,595,998 B2 | 7/2003 | Johnson et al. |
| 6,599,515 B1 | 7/2003 | Delmotte |
| 6,616,698 B2 | 9/2003 | Scarborough |
| 6,618,698 B1 | 9/2003 | Beausoleil et al. |
| 6,623,749 B2 | 9/2003 | Williams et al. |
| 6,648,919 B2 | 11/2003 | Ferree |
| 6,696,073 B2 | 2/2004 | Boyce et al. |
| RE38,522 E | 5/2004 | Gertzman et al. |
| 6,740,093 B2 | 5/2004 | Hochschuler et al. |
| 6,752,831 B2 | 6/2004 | Sybert et al. |
| 6,783,546 B2 | 8/2004 | Zucherman |
| 6,843,807 B1 | 1/2005 | Boyce et al. |
| 6,884,428 B2 | 4/2005 | Binette et al. |
| 6,884,778 B2 | 4/2005 | Jo et al. |
| 6,911,212 B2 | 6/2005 | Gertzman et al. |
| 6,953,594 B2 | 10/2005 | Lee et al. |
| 6,969,404 B2 | 11/2005 | Ferree |
| 6,989,029 B2 | 1/2006 | Bonutti |
| 7,001,390 B2 | 2/2006 | Gebhardt et al. |
| 7,008,591 B2 | 3/2006 | Kafesjian et al. |
| 7,019,192 B2 | 3/2006 | Gertzman et al. |
| 7,025,771 B2 | 4/2006 | Kuslich et al. |
| 7,045,141 B2 | 5/2006 | Merboth et al. |
| 7,060,287 B1 | 6/2006 | Hubbard et al. |
| 7,108,832 B2 | 9/2006 | Christensen et al. |
| 7,163,691 B2 | 1/2007 | Knaack et al. |
| 7,179,299 B2 | 2/2007 | Edwards et al. |
| 7,208,015 B2 | 4/2007 | Pointillart et al. |
| 7,220,282 B2 | 5/2007 | Kuslich |
| 7,226,481 B2 | 6/2007 | Kuslich |
| 7,241,303 B2 | 7/2007 | Reiss et al. |
| 7,261,720 B2 | 8/2007 | Stevens et al. |
| 2001/0031254 A1 | 10/2001 | Bianchi et al. |
| 2001/0043258 A1 | 11/2001 | Ohki |
| 2002/0058947 A1 | 5/2002 | Hochschuler et al. |
| 2002/0068974 A1 | 6/2002 | Kuslich et al. |
| 2002/0077701 A1 | 6/2002 | Kuslich |
| 2002/0133166 A1 | 9/2002 | McKay et al. |
| 2002/0197297 A1 | 12/2002 | Risbud et al. |
| 2003/0008328 A1 | 1/2003 | Wironen et al. |
| 2003/0039676 A1 | 2/2003 | Boyce et al. |
| 2003/0044445 A1 | 3/2003 | Kay et al. |
| 2003/0065392 A1 | 4/2003 | Fan et al. |
| 2003/0072677 A1 | 4/2003 | Kafesjian et al. |
| 2003/0129178 A1 | 7/2003 | Wegman et al. |
| 2003/0143258 A1 | 7/2003 | Knaack et al. |
| 2003/0152548 A1 | 8/2003 | Mikos et al. |
| 2003/0194708 A1 | 10/2003 | Binnerts et al. |
| 2004/0023387 A1 | 2/2004 | Morris et al. |
| 2004/0024457 A1 | 2/2004 | Boyce et al. |
| 2004/0059364 A1 | 3/2004 | Gaskins et al. |
| 2004/0072322 A1 | 4/2004 | Thorne |
| 2004/0146543 A1 | 7/2004 | Shimp et al. |
| 2004/0220615 A1 | 11/2004 | Lin |
| 2004/0249464 A1 | 12/2004 | Bindseil et al. |
| 2005/0008620 A1 | 1/2005 | Shimp et al. |
| 2005/0008672 A1 | 1/2005 | Winterbottom et al. |
| 2005/0020506 A1 | 1/2005 | Drapeau et al. |
| 2005/0027033 A1 | 2/2005 | Knaack et al. |
| 2005/0037978 A1 | 2/2005 | Damien |
| 2005/0131417 A1 | 6/2005 | Ahern et al. |
| 2005/0244450 A1 | 11/2005 | Reddi |
| 2005/0244457 A1 | 11/2005 | Reddi |
| 2005/0251267 A1 | 11/2005 | Winterbottom et al. |
| 2005/0283255 A1 | 12/2005 | Geremakis et al. |
| 2006/0216321 A1 | 9/2006 | Lyu et al. |
| 2006/0216323 A1 | 9/2006 | Knaack et al. |
| 2006/0287732 A1 | 12/2006 | Pezeshkian |
| 2007/0073401 A1 | 3/2007 | Pointillart et al. |
| 2007/0093896 A1 | 4/2007 | Malinin |
| 2007/0098756 A1 | 5/2007 | Behnam |
| 2007/0110820 A1 | 5/2007 | Behnam |
| 2007/0118222 A1 | 5/2007 | Lang |
| 2007/0125700 A1 | 6/2007 | Ding et al. |
| 2007/0142916 A1 | 6/2007 | Olson et al. |
| 2007/0154563 A1 | 7/2007 | Behnam et al. |
| 2007/0162132 A1 | 7/2007 | Messerli |
| 2007/0178158 A1 | 8/2007 | Knaack et al. |
| 2007/0231788 A1 | 10/2007 | Behnam et al. |
| 2008/0027546 A1 | 1/2008 | Semler et al. |
| 2008/0069852 A1 | 3/2008 | Shimp et al. |
| 2008/0091270 A1 | 4/2008 | Miller et al. |
| 2008/0260794 A1 | 10/2008 | Lauritzen et al. |
| 2009/0087471 A1 | 4/2009 | Shimp et al. |
| 2009/0130173 A1 | 5/2009 | Behnam et al. |
| 2009/0155378 A1 | 6/2009 | Behnam et al. |
| 2009/0157087 A1 | 6/2009 | Wei et al. |
| 2009/0192474 A1 | 7/2009 | Wei et al. |
| 2009/0220605 A1 | 9/2009 | Wei et al. |

FOREIGN PATENT DOCUMENTS

| | | |
|---|---|---|
| EP | 0 082 621 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 0 603 920 A1 | 6/1994 |
| EP | 0 621 020 A1 | 10/1994 |
| EP | 0781564 A2 | 7/1997 |
| JP | 01/179689 | 7/1989 |
| WO | 88/00205 | 1/1988 |
| WO | 88/01517 | 3/1988 |
| WO | 90/03733 | 4/1990 |
| WO | 94/21298 | 9/1994 |
| WO | 95/31948 | 11/1995 |
| WO | 96/39170 | 12/1996 |
| WO | 00/13615 | 3/2000 |
| WO | 00/45870 | 8/2000 |
| WO | 00/47736 | 8/2000 |
| WO | 01/28461 A2 | 4/2001 |
| WO | 01/70136 A2 | 9/2001 |
| WO | 01/79342 A2 | 10/2001 |
| WO | 02/69818 A2 | 9/2002 |
| WO | 03/025271 A1 | 3/2003 |
| WO | 03/030956 A3 | 4/2003 |
| WO | 2004/073563 A | 9/2004 |

| | | |
|---|---|---|
| WO | 2005/065396 A2 | 7/2005 |
| WO | 2005/072656 A1 | 8/2005 |
| WO | 2005/081699 A2 | 9/2005 |
| WO | 2006/076712 | 7/2006 |
| WO | 2007/053850 | 5/2007 |
| WO | 2007/133451 | 11/2007 |

OTHER PUBLICATIONS

Bolander et al., "The Use of Demineralized Bone Matrix in the repair of Segmental Defects", The Journal of Bone and Joint Surgery, 68-A (8): 1264-1273.

Bravo, D.A. et al., "Accurate and Efficient Cleavage of the Human Insulin Proreceptor by the Human Proprotein-Processing Protease Furin," Journal Biol. Chern.269: 25830-25873 (1994).

Cameron, A. et al., "Polyarginines are potent inhibitors," J. Bioi. Chern. 275:36741-36749 (2000).

Canalis et al., "Stimulation of DNA and Collagen Synthesis by Autogous Growth Factor in Cultured Fetal Rat Calvaria," Science, 210:1021-1023 (1980).

Caplanis et al., "Effect of allogenic freeze-dried demineralized bone matrix on guided tissue regeneration in dogs," J. Periodontal, 851-856 (Aug. 1998).

Constantino, et al. "Bone Healing and Bone Substitutes," Facial Plastic Surgery 18(1): pp. 14-26 (2002).

Crowe et al., "Inhibition of Enzymatic Digestion of Amylose by Free Fatty Acids in Vitro Contributes to Resistant Starch Formation", J. Nutr., 130(8): 2006-2008 (2000).

Cui et al., "The activity and signaling range of mature BMP-4 is regulated by sequential cleavage at two sites within the prodomain of the precursor," Genes and Development,15:2797-2802 (2001).

Cui et al., "BMP-4 is proteolytically activated by furin and/or PC6 during vertebrae embryonic development," The Embo Journal, 17(16):4735-4743 (1998).

Deatherage et al., "Packaging and Delivery of Bone Induction Factors in a Collagenous Implant," Collagen Rei. Res. 7:225-231 (1987).

Driessens et al., "Calcium Phosphate Bone Cements," Universitat Politecnica de Catalunya, Barcelona, Spain, 31:855-77.

Dubois et al., "Evidence that Furin is an Authentic Transforming Growth Facto-B-1-Converting Enzyme," American Journal of Pathology, 158(1):305-316 (2001).

Farley et al., "Human Skeletal Growth Factor: Characterization of the Mitogenic Effect on Bone Cells in Vitro," Biochem, 21:3508-3513 (1982).

Flemmig, et al. "Long-Term Maintenance of Alveolar Bone Gain After Implantation of Autolyzed, Antigen-Extracted, Allogenic Bone in Periodontal Intraosseous Defects," J. Periodontal, 69(1): 47-53 (Jan. 1998).

Gamradt, et al. "Bone Gaft for Revision Hip Arthroplasty", Clin. Ortho. and Related Research, 417: 183-194 (2003).

Gepstein et al. "Bridging Large Defects in Bone by Demineralized Bone Matrix in the Form of a Powder," The Journal of Bone and Joint Surgery, 69A(7): 984-991 (1987).

Glowacki, "Cellular Reactions to Bone-Derived Material," Clin. Ortho. and Related Research, 324: 47-54 (1996).

Glowacki, "Fate of Mineralized and Demineralized Osseous Implants in Cranial Defects," Calcif. Tissue Int., 33:71-76 (1981).

Glowacki et al., "Demineralized bone implants," Symposium on Horizons in Plastic Surgery, 12(2): 233-41 (1985).

Han B., et al., "Quantitive and sensitive in vitro assay for osteoinductive activity of demineralized bone matrix," J. Orthop. Res. 21(4): 648-54 (Jul. 2003).

Han, C. et al. "Autolysed Antigen-Extracted Allogeneic Bone for Repair of Diaphyseal Bone Defects in Rabbits," Yonsei Medical Journal, 31(3):251-257 (1990).

Hollinger, et al. "A comparison of four particulate bone derivatives," Clin. Ortho. and Related Research, 267: 255-263 (Jun. 1991).

Hunziker et al., "Repair of Partial Thickness Defects in Articalte Cartilage: Cell Recruitment from the Synovial Membrane", Journal Bone Joint Surg., 78-A: 721-733 (1996).

Iwata et al. "Chemosterilized Autolyzed Antigen-Extracted Allogeneic (AAA) Bone Matrix Gelatin for Repair of Defects from Excision of Benign Bone Tumors," Clin. Ortho and Related Research, 154: 150-155 (1981).

Jain et al., "Anchoring of phospholipase A2: the effect of anions and deuterated water, and the role of N-terminus region," Biochem. Et Biophys. Acta, 860:448-461 (1986).

Janovec, et al. "Autolyzed Antigen-Extracted Allogeneic Bone for Bridging Segmented Diaphyseal Bone Defects in Rabbits," Clin. Ortho. and Related Research, 229: 249-256 (Apr. 1988).

Jean et al., "Alpha 1-Antitrypsin Portland, a bioengineered serpin highly selective for furin: Application as an antipathogenic agent", Proc. Natl. Acad. Sci., USA 95: 7293-7298 (1998).

Johnson et al. "Human Bone Mortphogenetic Protein Allografting for Reconstruction of Femoral Nonunion," Clin. Ortho. and Related Research, 371: 61-74 (2000).

Johnson et al. "Preliminary explorations of reconstructive surgery with implants of autolyzed antigen-extracted allogeneic (AAA) bone supercharged with bone morphogenetic protein (BMP)," Bone Grafts, Derivatives and Substitutes, published by Butterworth-Heinemann, Oxford, pp. 363-376 (1994).

Johnson et al. "Resistant Nonunions and Partial or Complete Segmental Defects of Long Bones," Clin. Ortho. and Related Research, 277: 229-237 (Apr. 1992).

Kaban et al., "Treatment of Jaw Defects with Demineralized Bone Implants", Journal of Oral and Maxillofacial Surgery, pp. 623-626 (Jun. 6, 1989).

Katz, "The Biology of Heavy Water," Scientific American, 106-116 (1960).

Kawai et al., Clin. Orthopaedics and Related Res., 233: 262-267 (1988).

Krysan, D.J., et al., "Quantitive Characterization of Furin Specificity", Journal Bioi. Chern. 274, pp. 23229-23234 (1999).

Kubler et al. "Allogenic Bone & Cartilage Morphogenesis," J. Craniomaxillofac. Surg., 19(7): 283-288 (1991).

Kubler et al. "Osteoinductive, morphologic, and biomechanical properties of autolyzed, antigen-extracted, allogeneic human bone," J. Oral Maxillofac Surg, 51: 1346-1357 (1993).

Kubler et al. "Repair of human skull defects using osteoinductive bone alloimplants," J. of Crania Maxillofac. Surg. 23: 337-346 (1995).

Lee et al., Nature, 424: 389 (2003).

Lewandrowski et al., "Flexural Rigidity in Partially Demineralized Diaphyseal Bone Grafts", Clin, Ortho. Ref. Res., 317: 254-262 (1995).

Lewandrowski et al. "Mechanical Properties of Perforated and Partially Demineralized Bone Grafts," Clin. Ortho. and Related Research, 353: 238-246 (1998).

Lieberman, et al. "Treatment of Osteonecrosis of the Femoral Head with Core Decompression and Human Bone Morphogenetic Protein," Clin. Ortho. and Related Research, 429: 139-145 (2004).

Lotz, Clin. Orthopaedics and Related Res., 391S: S108-S115 (2001)

Mellonig, James. "Bone Allografts in Periodontal Therapy," Clin. Ortho. and Related Research, 324: 116-125 (1996).

Mellonig, "Decalcified freeze-dried bone allograft as an implant material in human periodontal defects," The Int'l Journal of Periodontics and Restorative Dentistry, pp. 41-45 (1984).

Miloslav et al., "Autolyzed antigen-extracted allogeneic bone for bridging segmented diaphyseal bone defects in rabbits," Clinical Orthopaedics and Related Research, 229: 249-256 (Apr. 1988).

Nade et al. "Decalcified Bone as a Substrate for Osteogenesis," Bone Joint Surg. 59(2): 189-1996 (1977).

Neigel et al. "Use of Demineralized Bone Impants in Orbital and Craniofacial Reconstruction and Review of the Literature," Opthal. Plast. Reconst. Surg., 12:108 (1996).

Nogami et al., "Sustrata Prepared from Bone Matrix for Chondrogenesis in Tissue Culture", The Journal of Cell Biology, 62: 510-519 (1974).

Nogami et al., "Transmembrane Bone Matrix Gelatin-Induced Differentiation of Bone", Calcif. Tiss. Res., 19: 153-163 (1975).

Oberg et al. "Bone formation after implantation of autolysed antigen extracted allogeneic bone in ovariectomized rabbits," Int. J. Oral Maxillofac. Surg. 32:628-632 (2003).

Oberg et al. "Bone healing after implantation of hydroxyapatite granules and blocks (Interpore 200) combined with autolyzed antigen-extracted allogeneic bone and fibrin glue," Int. J. Oral. Maxillofac. Surg. 23: 110-114 (1994).

Ousterhout. "Clinical Experience in Cranial and Facial Reconstruction with Demineralized Bone," Ann. Plast. Surg. 15(5): 367-373 (1995).
Paralkar et al., "An EP2 receptor-selective prostaglandin E2 agonist induces bone healing," PNAS, 100(11): 6736-6740 (2003).
Peel SA et al., "In search of the ideal bone morphogenetic protein delivery system: in vitro studies on demineralized bone matrix, purified, and recombinant bone morphogenetic protein", J. Craniofac. Surg., 14(3): 284-91 (May 2003).
Ray et al., "Bone Implants," J. Bone Joint Surgery, 39A(5): 119-1128 (1957).
Reddi et al., "Biochemical Sequences in the Transformation of Normal Fibroblasts in Adolescent Rats," Proc. Natl. Acad. Sci. USA, 69(6): 1601-1605 (1972).
Ripamonti et al. "Bone induction in a composite allogeneic bone/alloplastic implant," J. Oral Maxillofac. Surg. 47: 963-969 (1989).
Ripamonti et al. "The induction of bone in osteogenic composites of bone matrix and porous hydroxyapatite replicas: Experimental study on the baboon," Oral Maxillofac. Surg. 9: 817-830 (1991).
Ripamonti. "Bone induction in nonhuman primates: an experimental study on the baboon," Clin. Ortho. and Related Research, 269: 284-294 (Aug. 1991).
Ripamonti. "Calvarial regeneration in primates with autolyzed antigen-extracted allogeneic bone," Clin. Ortho. and Related Research, 282:293-303 (Sep. 1992).
Ronningen et al. "Bone formation enhanced by induction," Acta Orthop Scan 56: 67-71 (1985).
Ronningen et al. "Osteogenesis promoted by bone matrix combined with marrow," Acta Orthop Scand 5Z: 15-18 (1986).
Rosenquist et al. "Effects of bone grafting on maxillary bone healing in the growing pig," J. Oral Maillofac. Surg. 40: 566-569 (1982).
Rosenthal et al. "Demineralized bone implants for nonunion fractures, bone cysts, and fibrous lesions," Clin. Ortho. and Related Research 362: 61-69 (1999).
Russell et al., "Clinical Utility of Demineralized Bone Matrix for Osseous Defects, Arthrodesis, and Reconstruction; Impact of Processing Techniques and Study Methodology," Orthopaedics, 22(5): 524-531 (May 1999).
Sailer et al. "Application of purified bone morphogenetic protein (BMP) in crania-maxillo-facial surgery," Jour. of Cranio-Maxillo-Facial Surgery 22: 2-11 (1994).
Sampath and Reddi, "Homology of bone-inductive proteins from human, monkey, bovine, and rat extracellular matrix," Proc. Nat. Acad. Sci. 80:6591-6594 (1983).
Sampath et al., "Bovine osteogenic protein is composed of dimmers of OP-1 and BMP-2A, Two members of the transforming growth factor-beta superfamily," J. Bioi. Chem., 5:265(22): pp. 13198-13205 (Aug. 1990).
Sampath et al., "Isolation of osteogenin, an extracellular matrix-associated, bone-inductive protein, by heparin affinity chromatography," Proc. Natl. Acad. Sci. 84(7): 7109-7113 (1987).
Schmid et al. "Osteoinduction in tibial defects in the dog," Unfallchirurgie 19: 1-8 (1993).
Schwarz et al., "Dog bone less osteogenetic than rat bone," Acta. Orthop. Scan. 60(6): 693-695 (1989).
Schwarz et al. "Decalcified and undercalcified cancellous bone block implants do not heal diaphyseal defects in dogs," Arch. Orthop. Trauma Surg. 111:47-50 (1991).
Serini et al., "Class 3 semaphorins control vascular morphogenesis by inhibiting integrin function," Nature, 424:391-397 (Jul. 2003).
Steadman et al., "Microfracture: Surgical Technique and Rehabilitation to Treat Chondral Defects", Clin. Orthop., 391 S:362-369 (2001).
Steiner, D.F., "The proprotein convertases," Curr. Opinion Chern. Biol. 2: 31-39 (1998).
Temenoff et al., "Effect of poly(ethylene glycol) molecular weight on tensile and swelling properties of oligo(poly(ethylene glycol)fumarate) hydrogels for cartilage tissue engineering", OPF Hydrogel Material Properties, Joh Wiley & Sons, Inc., pp. 429-437 (2001).
Terashima et al., Chondrogenesis in Outgrowths of Muscle Tissue onto Modified Bone Matrix in Tissue Culture, Clinical Orthopaedics and Related Research, 127: 248-256 (Sep. 1977).

Todescan et al., "A Small Animal Model for Investigating Endosseous Dental Implants: Effect of Graft Materials on healing of Endoss, Porous-Surfaced Implants Placed in a Fresh Extraction Socket," The Journal of Oral and Maxillofacial Implants, 2(2): 217-223 (1987).
Toriumi et al. "Demineralized Bone," Arch Otolaryngol Head Neck Surg. 116: 676-680 (Jun. 1990).
Ueland et al., J. Clin. Endocrinol. & Metab., 84(1): 123-127 (1999).
Urist, "Bone: Formation by Autoinduction," Science, 150(698): pp. 893-899 (1965).
Urist, "The Bone Induction Principle," Clin. Ortho. Ref. Res., 55:243-283 (1967).
Urist et al., "Bone morphogenesis in Implants of Insoluble Bone Gelatin," Proc. Natl. Acad. Sci., 70(12): 3511-5 (Dec. 1973).
Urist et al., "Preservation and biodegradation of the morphogenetic of bone matrix," J. Theor. Biol. 38: 155-67 (1973).
Urist et al., "Observations implicating an extracellular enzymic mechanism of control of bone morphogenesis," J. Histochem & Cytochem, 22(2): 88-103 (1974).
Urist et al., "A Chemosterilized Antigen-Extracted Autodigested Alloimplant for Bone Banks," Arch Surg. vol. 110: 416-428 (Apr. 1975).
Urist et al., "Cartilage Tissue Differentiation from Mesenchymal Cells Derived from Mature Muscle in Tissue Culture", In Vitro, 14(8): 697-706 (1978).
Urist et al. "Intertransverse Process Fusion with Aid of Chemosterilized Autolyzed Antigen-Extracted Allogeneic (AAA) Bone," Clin. Ortho. and Related Research, 154:97-113 (1981).
Urist et al., "Human Bone Morphogenetic Protein (hBMP)," Proc. Soc. Exp. Biol. 173:194-199 (1983).
Urist et al., "Purification of bovine bone morphogenetic protein by hydroxyapatite chromatography," Prop. Natl. Acad. Sci. 81:371-375 (1984).
Van den Berg et al., "Tissue Engineering, Cells, Scaffolds, and Growth Factors," Clin. Orthopaedics and Related Res., 391S:S244-S250 (2001).
Van den Ouweland, A.M.W. et al., "Structural homology between the human fur gene product and the subtilisin-like protease encoded by yeast KEX2," Nucl. Acid Res. 18(3): 664 (1990).
Wang et al., "Purification and characterization of other distinct bone-inducing factors," Proc. Nat. Acad. Sci. 85:9484-9488 (1988).
Wang et al., "Recombinant human bone morphogenetic protein induces bone formation," Proc. Nat. Acad. Sci. 87:2220-2224 (1990).
White et al., "Effective terminal sterilization using supercritical carbon dioxide," Journal of Biotechnology, 123: 504-515 (2006).
Whiteman et al., "Demineralized Bone Powder," J. Hand. Surg. 18B(4): 487-490 (1993).
Whittaker et al., "Matrix Metalloproteinases and Their Inhibitors—Current Status and Future Challenges," Celltransmissions, 17(1): 3-14.
Xiaobo et al., "Experimental and Clinical Investigations of Human Insoluble Bone Matrix Gelatin," Clin. Orthopaedics and Related Research, 293: 360-365 (1993).
Young et al. "Morphological changes of autoclaved autogenic bone implantation and autoclaved autogenic bone supplemented with allogenic demineralized bone matrix in rat parietal bone," Histol Histopathol. 11: 361-369 (1996).
Zhang et al., "A Quantitative assessment of osteoinductivity of human demineralized bone matrix," J. Periodontal, 68(11): 1076-84 (Nov. 1997).
Lewandrowski et al. "Kinectics of cortical bone demineralization: controlled demineralization—a new method for modifying cortical bone allografts," J. Biomed Materials Res, 31: 365-372 (1996).
Lewandrowski et al., "An Electron Microscopic Study on the Process of Acid Demineralization of Cortical Bone," Calified Tiss. Int., 61: 294-297 (1997).
Lewandrowski et al., "Improved Osteoinduction of Cortical Bone Allografts: A Study of the Effects of Laser Perforation and Partial Demineralization", J. Ortho. Research, 15:748-756 (1997).
Enlow, Donald H., "Principle of Bone Remodeling: An Account of Post-natal Growth and remodeling Processes in Long Bones and the Mandible," Charles C. Thomas, Springfield, Ill., (1963).

Kasten, P. et al. "Comparison of human bone marrow stromal cells seeded on calcium-deficient hydroxyapatite, beta-tricalcium phosphate and demineralized bone matrix", Biomaterials 24: 293-2603 (2003).

Wise, D.L., "Encyclopedia Handbook of Biomaterials and Bioengineering Part B", Applicants New York: Marcel Decker (1995).

Elliott, J.C., "Structure and Chemistry of the Apatites and Other Calcium Orthophosphates", Elsevier Science B.V., Amsterdam (1994).

Canalis, Ernesto et al., "8one Morphogenetic Proteins, Their Antagonists, and the Skeleton", Endocrine Reviews, 24(2): 218-235 (2003).

Edwards, Jean T. et al. "Osteoinduction of Human Demineralized Bone: Characterization in a Rat Model", Clinical Orthopaedics and Related Research, 357:219-228 (1998).

Sambrook, et al. Molecular Cloning: A Laboratory Manual, 3rd ed., Cold Spring Harbor Laboratory Press, Cold Spring Harbor (2001).

Rodd, "Chemistry of Carbon Compounds", vols. 1-5 and supplementals, Elsevier Science Publishers, Amsterdan (1989).

"Organic Reactions", vols. 1-40, John Wiley and Sons, New York, NY (1991).

Smith, Michael et al. "March's Advanced Organic Chemistry", 5th edition, John Wiley and Sons, New York, NY (Mar. 2001).

Fujishiro et al., "Histological evaluation of an impacted bone graft substitute composed of a combination of mineralized and demineralized allograft in a sheep vertebral bone defect", Journal of Biomedical Materials Research Part A, (2007), pp. 538-544.

Landesman, Richard et al., "In Vivo Analysis of the Half-Life of the Osteoinductive Potential of Demineralized Bone Matrix Using Diffusion Chambers", Calcif. Tissue Int., vol. 345, No. 6 1989, 348-353.

Laursen, Malene et al., "Optimal Handling of freshcancellous bone graft—Different peroperative storing techniques evaluated by in vitro osteobalst-like cell metabolism", Acta Orthop Scand. vol. 74 No. 4 2003, 491.

Ou, Wenbin et al. "Effects of Glycerol in the Refolding and Unfolding of Creatine Kinase," Tsinghua Science and Technology, 7(4): 352-367 (Aug. 2002).

Ou, Wenbin et al. "Molecular Mechanism for Osmolyte Protection of Creatine Kinase Against Guanidine Denaturation," Eur. J. Biochem., 268: 5901-5911 (2001).

Lewandrowski et al., Bio-Med Material Eng 11:197-207, 2001.

Outer　　　Middle　　　Inner

OI Results

|  | Outer Layer | Middle Layer | Inner Layer |
|---|---|---|---|
| OI (Mean) | 3.17 | 2.50 | 1.83 |
| OI (SD) | 0.41 | 0.55 | 0.41 |
| # of Implants | 6 | 6 | 6 |
| p value (Kruskall Wallis) | 0.0087 | | |

DEMINERALIZED BONE MATRIX COMPOSITIONS AND METHODS

CROSS REFERENCE TO RELATED APPLICATIONS

This application is a continuation application of U.S. application Ser No. 12/254,619, filed on Oct. 20, 2008, now U.S. Pat. No. 8,202,539, which is hereby incorporated by reference in its entirety, which claims priority from U.S. 60/981,395 filed on Oct. 19, 2007.

FIELD OF THE INVENTION

The present invention relates generally to bone matrix compositions and more specifically to demineralized bone matrix having increased osteoinductive capacity and methods for its production.

BACKGROUND

Mammalian bone tissue is known to contain one or more proteinaceous materials, presumably active during growth and natural bone healing, that can induce a developmental cascade of cellular events resulting in endochondral bone formation. The active factors have variously been referred to in the literature as bone morphogenetic or morphogenic proteins (BMPs), bone inductive proteins, bone growth or growth factors, osteogenic proteins, or osteoinductive proteins. These active factors are collectively referred to herein as osteoinductive factors.

These osteoinductive factors are present within the compound structure of cortical bone and are present at very low concentrations, e.g., 0.003%. Osteoinductive factors direct the differentiation of pluripotent mesenchymal cells into osteoprogenitor cells that form osteoblasts. Based upon the work of Marshall Urist as shown in U.S. Pat. No. 4,294,753, issued Oct. 13, 1981, proper demineralization of cortical bone exposes the osteoinductive factors, rendering it osteoinductive, as discussed more fully below.

Overview of Bone Grafts

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous cancellous bone ("ACB"), also known as autograft or autogenous bone, is considered the gold standard for bone grafts. ACB is osteoinductive and nonimmunogenic, and, by definition, has all of the appropriate structural and functional characteristics appropriate for the particular recipient. Unfortunately, ACB is only available in a limited number of circumstances. Some individuals lack ACB of appropriate dimensions and quality for transplantation, and donor site pain and morbidity can pose serious problems for patients and their physicians.

Bone grafting applications may be differentiated by the requirements of the skeletal site. Certain applications require a "structural graft" in which one role of the graft is to provide mechanical or structural support to the site. Such grafts contain a substantial portion of mineralized bone tissue to provide the strength needed for load-bearing. Examples of applications requiring a "structural graft" include intercalary grafts, spinal fusion, joint plateaus, joint fusions, large bone reconstructions, etc. Other applications require an "osteogenic graft" in which one role of the graft is to enhance or accelerate the growth of new bone tissue at the site. Such grafts contain a substantial portion of demineralized bone tissue to improve the osteoinductivity needed for growth of new bone tissue. Examples of applications requiring "osteogenic graft" include deficit filling, spinal fusions, joint fusions, etc. Grafts may also have other beneficial biological properties such as, for example, serving as delivery vehicles for bioactive substances. Bioactive substances include physiologically or pharmacologically active substances that act locally or systemically in the host.

The biomechanical properties of osteoimplants upon implantation are determined by many factors, including the specific site from which the bone used to make the osteoimplant is taken; various physical characteristics of the donor tissue; and the method chosen to prepare, preserve, and store the bone prior to implantation, as well as the type of loading to which the graft is subjected.

Much effort has been invested in the identification and development of alternative bone graft materials. Urist published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. DBM is an osteoinductive material in that it induces bone growth when implanted in an ectopic site of a rodent, at least partially because of the osteoinductive factors contained within the DBM. Honsawek et al. (2000). It is now known that there are numerous osteoinductive factors, e.g., BMP2, BMP4, BMP6, BMP7, which are part of the transforming growth factor-beta (TGF-beta) superfamily (Kawabata et al., 2000). BMP-2 has become the most important and widely studied of the BMP family of proteins. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta.1) (Hauschka, et al. 1986; Canalis, et al, 1988; Mohan et al. 1996).

Accordingly, a known technique for promoting the process of incorporation of osteoimplants is demineralization over outer surfaces, inner surfaces, or the entire volume of the implant. The process of demineralizing bone grafts is well known. In this regard see, Lewandrowski et al., J. Biomed Materials Res, 31, pp. 365 372 (1996); Lewandrowski et al., Calcified Tiss. Int., 61, pp. 294 297 (1997); Lewandrowski et al., J. Ortho. Res., 15, pp. 748 756 (1997), the contents of each of which is incorporated herein by reference.

DBM implants have been reported to be particularly useful (see, for example, U.S. Pat. Nos. 4,394,370, 4,440,750, 4,485,097, 4,678,470, and 4,743,259; Mulliken et al., Calcif Tissue Int. 33:71, 1981; Neigel et al., Opthal. Plast. Reconstr. Surg. 12:108, 1996; Whiteman et al., J. Hand. Surg. 18B:487, 1993; Xiaobo et al., Clin. Orthop. 293:360, 1993, each of which is incorporated herein by reference). DBM typically is derived from cadavers. The bone is removed aseptically and treated to kill any infectious agents. The bone is particulated by milling or grinding, and then the mineral component is extracted by various methods, such as by soaking the bone in an acidic solution. The remaining matrix is malleable and can be further processed and/or formed and shaped for implantation into a particular site in the recipient. The demineralized bone particles or fibers can be formulated with biocompatible excipients to enhance surgical handling properties and conformability to the defect or surgery site. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

BRIEF SUMMARY

Bone matrix compositions and, more specifically, demineralized bone matrix (DBM) having increased osteoinductive capacity and methods for its production are provided. The periosteum is a layer of connective tissue membrane that covers the outer surface of bone. The endosteum is a layer of connective tissue which lines the surface of bony tissue that forms the medullary cavity of long bones. Accordingly, the outer/periosteal layer of bone may be referred to as the periosteal layer of bone and the inner/endosteal layer of bone may be referred to as the endosteal layer of bone. In some embodiments, DBM derived from cortical bone from the periosteal layer of bone are provided. Preparations of and methods of use of DBM compositions and, more specifically, DBM compositions from the periosteal layer of bone, are disclosed.

In accordance with one embodiment, a demineralized bone matrix composition comprising a disproportionate percentage of cortical bone derived from a periosteal layer is provided.

In accordance with another embodiment, an allograft composition comprising demineralized bone matrix wherein the demineralized bone matrix is comprised of a disproportionate percentage of cortical bone derived from a periosteal layer is provided.

In accordance with yet another embodiment, a demineralized bone matrix composition comprising a disproportionate percentage of demineralized bone derived from bone from a periosteal layer is provided. The demineralized bone matrix composition has no exogenous growth factor or DBM extract. The demineralized bone matrix composition has an osteoinductive factor content greater than demineralized bone matrix comprising bone derived from non-periosteal layer sources.

In accordance with a further embodiment, a method for producing an osteoinductive composition is provided. The method comprises obtaining cortical bone comprising a disproportionate percentage of demineralized bone from a periosteal layer and demineralizing the cortical bone.

In accordance with yet a further embodiment, a method for producing an osteoinductive composition is provided comprising milling bone from a periosteal layer, milling bone from a middle layer, and milling bone from an endosteal layer. The bone milled from the periosteal layer is separated and demineralized. A composition is formed with the demineralized bone from the periosteal layer and has a disproportionate amount of bone from the periosteal layer.

This application refers to various patents, patent applications, journal articles, and other publications, all of which are incorporated herein by reference. The following documents are incorporated herein by reference: U.S. patent applications Ser. Nos. 11/555,606 and 11/555,608; PCT/US04/43999; PCT/US05/003092; U.S. Pat. No. 7,163,691 A1; PCT/US02/32941; *Current Protocols in Molecular Biology, Current Protocols in Immunology, Current Protocols in Protein Science*, and *Current Protocols in Cell Biology*, John Wiley & Sons, N.Y., edition as of July 2002; Sambrook, Russell, and Sambrook, *Molecular Cloning: A Laboratory Manual*, 3rd ed., Cold Spring Harbor Laboratory Press, Cold Spring Harbor, 2001; Rodd 1989 "Chemistry of Carbon Compounds," vols. 1-5 and Supps, Elsevier Science Publishers, 1989; "Organic Reactions," vols 1-40, John Wiley and Sons, New York, N.Y., 1991; March 2001, "Advanced Organic Chemistry," 5th ed. John Wiley and Sons, New York, N.Y. In the event of a conflict between the specification and any of the incorporated references, the specification shall control. Where numerical values herein are expressed as a range, endpoints are included.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

DEFINITIONS

Figure 1A:
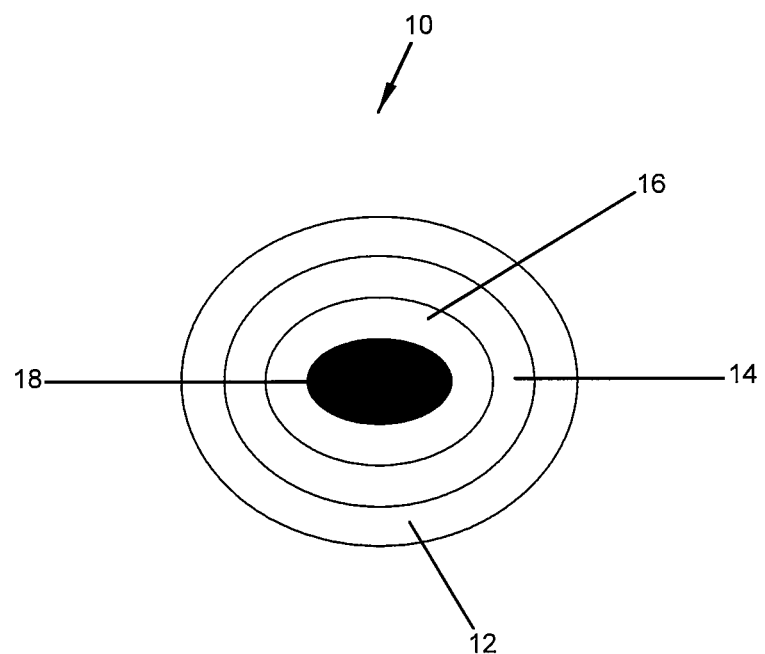
FIG. 1a illustrates a cross-section of a long bone showing the periosteal layer, middle layer, and endosteal layer of cortical bone.

Bioactive Agent or Bioactive Compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, mitotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD the abbreviation for the amino acid sequence Arginine-Glycine-Aspartic acid. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

Biocompatible, as used herein, describes materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium. In some embodiments, the demineralized compositions may comprise less than 1% calcium by weight. Partially demineralized bone is intended to refer to preparations with greater than 5% calcium by weight but containing less than 100% of the original starting amount of calcium. In some embodiments, demineralized bone has less than 95% of its original mineral content. "Demineralized" is intended to encompass such expressions as "substantially demineralized," "partially demineralized," "surface demineralized," and "fully demineralized." "Partially demineralized" is intended to encompass "surface demineralized."

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoimplant, as used herein, refers to any implant prepared in accordance with the embodiments described herein and therefore may include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.*, 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

Stabilizing agent, as used herein, refers to any chemical entity that, when included in a composition comprising bone matrix and/or a growth factor, enhances the osteoinductivity of the composition as measured against a specified reference sample or any entity that prolongs the shelf-life of DBM as compared to hydrated carriers. In most cases, the reference sample will not contain the stabilizing agent, but in all other respects will be the same as the composition with stabilizing agent. The stabilizing agent also generally has little or no osteoinductivity of its own and works either by increasing the half-life of one or more of the active entities within the composition as compared with an otherwise identical composition lacking the stabilizing agent, or by prolonging or delaying the release of an active factor. In certain embodiments, the stabilizing agent may act by providing a barrier between proteases and sugar-degrading enzymes thereby protecting the osteoinductive factors found in or on the matrix from degradation and/or release. In other embodiments, the stabilizing agent may be a chemical compound that inhibits the activity of proteases or sugar-degrading enzymes. In some embodiments, the stabilizing agent retards the access of enzymes known to release and solubilize the active factors. Half-life may be determined by immunological or enzymatic assay of a specific factor, either as attached to the matrix or extracted there from. Alternatively, measurement of an increase in osteoinductivity half-life, or measurement of the enhanced appearance of products of the osteoinductive process (e.g., bone, cartilage or osteogenic cells, products or indicators thereof) is a useful indicator of stabilizing effects for an enhanced osteoinductive matrix composition. The measurement of prolonged or delayed appearance of a strong osteoinductive response will generally be indicative of an increase in stability of a factor coupled with a delayed unmasking of the factor activity.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

DETAILED DESCRIPTION

Milled periosteal cortical bone and compositions and implants comprising milled periosteal cortical bone and, in some embodiments, milled endosteal cortical bone, and methods for their production, are provided. The periosteum is a layer of connective tissue membrane that covers the outer surface of bone. The endosteum is a layer of connective tissue which lines the surface of bony tissue that forms the medullary cavity of long bones. Accordingly, the outer layer of bone may be referred to as the periosteal layer of bone and the inner layer of bone may be referred to as the endosteal layer of bone. A portion of bone is present between the periosteal layer of bone and the endosteal layer of bone. This portion may be referred to as one or more middle layers. Preparations of and methods of use of DBM compositions and, more specifically, DBM compositions comprising a disproportionate percentage of bone from the periosteal layer of bone and/or the middle layer of bone, are disclosed.

Milled bone obtained from different layers of cortical long bone having differing levels of osteoinductive capabilities. Referring to FIG. 1a, bone milled from the periosteal layer 12 of cortical bone 10 has increased osteoinductive capabilities compared with bone milled from middle layers 14 and the endosteal layer 16 of cortical bone 10. Accordingly, when periosteal bone is used to prepare demineralized bone matrix (DBM), the osteoinductive capability of the periosteal derived DBM is greater than DBM prepared with either endosteal or mediosteal derived or mixed DBM. Preparations of and methods for preparing and using such periosteal DBM compositions are described.

Cortical bone is a composite of growth zones that are reconstituted, rearranged, and relocated during growth and continued remodeling alterations. Bone tissues, including endosteal and periosteal deposits, migrate with age and bone remodeling. As discussed in *Principles of Bone Remodeling*, growth proceeds in length by endochondral bone replacement of the proliferating epiphyseal cartilage. The intramembranous bone of the cortex, both endosteal and periosteal, keeps pace in a longitudinal as well as a lateral direction with this linear growth of the cartilage plate. Donald H. Enlow, Ph.D., *Principles of Bone Remodeling*, 109-112 (Charles C. Thomas 1963).

In accordance with some embodiments, a DBM composition that is substantially derived from bone from the outer/periosteal layer of cortical bone is provided. In some embodiments, a composition comprising a mix of DBM particles prepared with bone derived from the outer/periosteal layer of cortical bone and DBM fibers prepared with bone derived from the interior/endosteal and/or middle layer of cortical bone is provided. In other embodiments, a composition comprising a mix of DBM fibers prepared with bone derived from the outer/periosteal layer of cortical bone and surface demineralized particles prepared with bone derived from the interior and/or middle layers of cortical bone is provided. In some embodiments, a DBM composition substantially free of the cortical bone derived from endosteal layer is provided. Further, in some embodiments, the bone particles may be divided into particles obtained from the endosteal layer and particles obtained from other sources wherein the particles obtained from the endosteal layer are used for applications where osteoinductivity is desirable and particles obtained from other sources are used for other applications.

In various embodiments, a composition or product may be provided comprising a disproportionate percentage of bone from the periosteal layer. A disproportionate amount of bone from any given layer is an amount of bone from that layer exceeding the amount one would expect if the entire bone were milled. This value, in some embodiments, may be considered as a ratio of bone from that layer to bone from other layers. In some embodiments, a whole bone may be considered as comprising three layers. When considering a whole bone as comprising approximately one third endosteal layer, approximately one third middle layer, and approximately one third periosteal layer, described more fully below, if the whole bone was milled, it would be expected that approximately one third of the milled bone would be from the periosteal layer. Thus, in accordance with some embodiments, a composition or product may be provided comprising with a disproportionate amount of bone from the periosteal layer, or in excess of approximately one third bone from the periosteal layer. In accordance with some embodiments, a composition or product may be provided comprising a disproportionate amount of bone from the periosteal and middle layers, or in excess of approximately two thirds bone from the periosteal layer and the middle layer. In yet further embodiments, a composition or product comprising a disproportionate amount of bone not from the endosteal layer, or less than approximately one third bone from the endosteal layer.

In some embodiments, the DBM composition may include growth enhancing compounds or compositions such as TGF-beta extract, bone mineral extract, tissue derived extract, peptide hormones, and combinations thereof. In other embodiments, the DBM composition may include growth factors such as cytokines, peptide hormones, bone mineral proteins, and the like. In other embodiments, the DBM composition may include excipients and/or carriers. Such excipients and carriers may include, for example, acetyltriethyl citrate (ATEC), acetyltri-n-butyl citrate (ATBC), aspartame and lactose, alginates, carbopol, carrageenan, lactose, lauryl lactate, methyl cellulose, guar gum, polyvinyl acetate phathalate, xanthan gum, and the like.

I. Introduction

A number of endogenous factors that play roles in the development and/or repair of bone and/or cartilage have been identified. BMPs such as BMP-2 and BMP-4 induce differentiation of mesenchymal cells towards cells of the osteoblastic lineage, thereby increasing the pool of mature cells, and also enhance the functions characteristic of differentiated osteoblasts. Canalis et al., *Endocrine Rev.* 24(2):218-235, 2003. In addition, BMPs induce endochondral ossification and chondrogenesis. BMPs act by binding to specific receptors, which results in phosphorylation of a class of proteins referred to as SMADs. Activated SMADs enter the nucleus, where they regulate transcription of particular target genes. BMPs also activate SMAD-independent pathways such as those involving Ras/MAPK signaling. Unlike most BMPs such as BMP-2 and BMP-4, certain BMPs (e.g., BMP-3) act as negative regulators (inhibitors) of osteogenesis. In addition, BMP-1 is distinct both structurally and in terms of its mechanism of action from other BMPs, which are members of the TGF-β superfamily. Unlike certain other BMPs (e.g., BMP-2, BMP-4), BMP-1 is not osteoinductive. Instead, BMP-1 is a collagenolytic protein that has also been shown to cleave chordin (an endogenous inhibitor of BMP-2 and BMP-4). Tolloid is a metalloprotease that is structurally related to BMP-1 and has proteolytic activity towards chordin See Canalis, supra, for further details regarding the activities of BMPs and their roles in osteogenesis and chondrogenesis.

Recently, the role of peptide hormones in the regeneration and growth of collagen and bone has been studied. See, for example, U.S. patent application Publication No. 20060247156, hereby incorporated by reference in its entirety. Such hormones, including, for example, calcitonin gene-related peptide (CGRP), cholecystokinin (CCK), dynorphin, enkephalin, galanin, neuropeptide Y (NPY), neurotensin, somatostatin, substance P (SP), thyrotropin-releasing hormone (TRH), vasoactive intestinal peptide (VIP) were origninally identified due to their neurogenic actions. However, it has been found that many neuropeptides have anabolic, osteogenic and/or chondrogenic actions.

A variety of endogenous inhibitors of BMPs have been discovered in addition to chordin. These proteins act as BMP antagonists and include pseudoreceptors (e.g., Bambi) that compete with signaling receptors, inhibitory SMADs that block signaling, intracellular binding proteins that bind to activating SMADs, factors that induce ubiquitination and proteolysis of activating SMADs, and extracellular proteins that bind BMPs and prevent their binding to signaling receptors. Among the extracellular proteins are noggin, chordin, follistatin, members of the Dan/Cerberus family, and twisted gastrulation.

II. Implantable Osteoinductive DBM Compositions

An implantable osteoinductive DBM composition and methods for preparing such composition are provided. As illustrated in the examples contained herein, DBM derived from cortical long bone and taken from the periosteal layer has an increased biological activity when compared to DBM derived from a middle layer of the bone and, in turn, DBM derived from a middle layer of the bone has an increased biological activity when compared to DBM taken from the endosteal layer of the bone. Accordingly, DBM compositions provided herein may comprise a disproportionate amount of bone derived from the outer and/or middle layers of a cortical bone. The DBM composition provided herein may include other components such as carriers, growth factors, excipients, or the like, and may be formed into an implant and/or may be provided in a containment device.

The biological activities of the DBM composition provided herein that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, and exocytosis or endocytosis-inducing activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

III. Provide Bone Particles

Bone is provided for milling into particles. The bone may be autogenic, allogenic, xenogenic, or transgenic. Generally, the compositions provided herein derive from cortical bone. More specifically, the compositions provided herein typically derive from the shaft of long bones. In some embodiments, however, the compositions may derive from other cortical bone structures such as the flat bones of the skull or the surfaces of the ilium. Further, as may be appreciated by one skilled in the art, there may be instances where the teachings provided herein may be applied to cancellous bone.

Figure 1B:
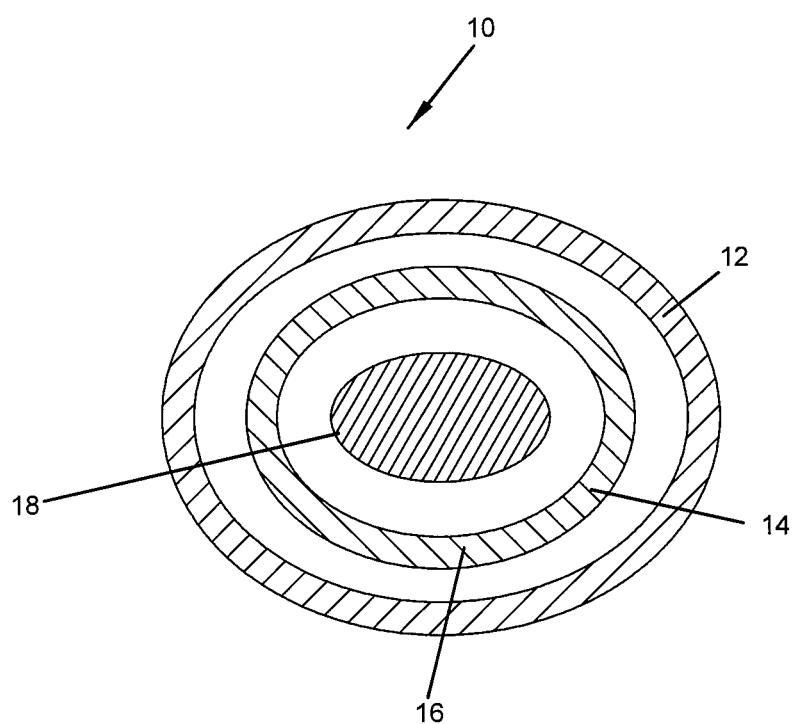
FIG. 1b illustrates a cross-section of a long bone showing the periosteal layer, middle layer, and endosteal layer of cortical bone with layers provided therebetween.

In some embodiments, the bone particles may be milled from different layers on the bone. For example, using a cortical long bone, the bone particles may be obtained from the periosteal layer (outer layer), from a middle layer, or from the endosteal layer (inner/endosteal layer). In accordance with the teachings herein, it has been discovered that DBM formed from bone taken from the periosteal layer has higher osteoinductive activity than DBM formed from bone taken from the middle layer or endosteal layer. FIG. 1a illustrates bone layers 12, 14, 16 of a cortical long bone 10. It is noted that FIG. 1a is not drawn to scale. An outer/periosteal layer 12, referred to as the periosteal layer, is present in the under the dense fibrous membrane (periosteum) that covers the outer surface of the bone. A middle layer 14 of cortical bone is found interior to the periosteal layer and an inner/endosteal layer 16, referred to as the endosteal layer, is found in the interior of the long bone 10 surrounding the marrow cavity 18. The depth of the outer/periosteal layer 12, the middle layer 14, and the inner/endosteal layer 16 may be determined as a percentage of the bone depth or may be determined as specific value. In one embodiment, the outer/periosteal layer extends from the outer surface of the bone to about 1.5 mm in depth, the middle layer extends from about 1.5 mm in depth to about 3 mm in depth, and the inner/endosteal layer extends from about 3 mm in depth to about 4.5 mm in depth. These valued are for the purposes of illustration only and the values will vary based on, at least, the size of the bone. In another embodiment, the outer/periosteal layer comprises approximately one third of the depth of the bone, the middle layer comprises approximately one third of the depth of the bone, and the inner/endosteal layer comprises approximately one third of the depth of the bone. While in some embodiments, the bone is considered as having three layers, it is to be appreciated that the bone may be considered to have more or fewer than three layers. For example, in the embodiment of FIG. 1b, a layer, the outer-middle layer, may be considered between the outer/periosteal layer and the middle layer and another layer, the inner-middle layer, may be considered between the middle layer and the inner/endosteal layer. When considering five layers in the bone, each layer may comprise approximately 20% of the bone depth or approximately 1-1.5 mm. Further, in some embodiment, the bone may be considered as having only two layers, an inner/endosteal layer and an outer/periosteal layer, where each layer comprises approximately 50% of the bone depth or approximately 2-4.5 mm.

Generally, it is to be appreciated that the bone, and the osteoinductivity of the bone, transitions from the inner/endosteal layer to the outer/periosteal layer. Thus, the exact percentages of the bone attributed to the inner/endosteal layer, the middle layer, and the outer/periosteal layer may vary and the 30% or 20% percentages are intended only to be illustrative of some layer values. Further, while in accordance with a specific embodiment, the periosteal layer comprises approximately the outer 1.5 mm of the bone, the middle layer comprises approximately the middle 1.5 mm of the bone, and the endosteal layer comprises approximately the inner 1.5 mm of the bone, it is to be appreciated that these values are from a particular example and apply to a bone of specific dimensions and these values will vary depending on the age of the bone, the location of the bone (e.g., whether femur, humerus, or other), and the thickness of the bone.

In various embodiments, a composition or product may be provided comprising a disproportionate percentage of bone from the periosteal layer. When considering a whole bone as comprising approximately one third endosteal layer, approximately one third middle layer, and approximately one third periosteal layer, if the whole bone was milled, it would be expected that approximately one third of the milled bone would be from the periosteal layer. Thus, in accordance with some embodiments, a composition or product may be provided comprising in excess of approximately one third bone from the periosteal layer. Similarly, in some embodiments, a composition or product may be provided comprising in excess of approximately two thirds bone from the periosteal and middle layers. Further, when considering whole bone as comprising five layers with approximately 20% of the depth of the bone being in the periosteal layer, if the whole bone was milled, it would be expected that approximately 20% of the milled bone would be from the periosteal layer. Thus, in accordance with some embodiments, a composition or product may be provided comprising in excess of approximately 20% bone from the periosteal layer. Similarly, in some embodiments, a composition or product may be provided comprising in excess of approximately 60% bone from the periosteal layer and middle layers.

Figure 1C:
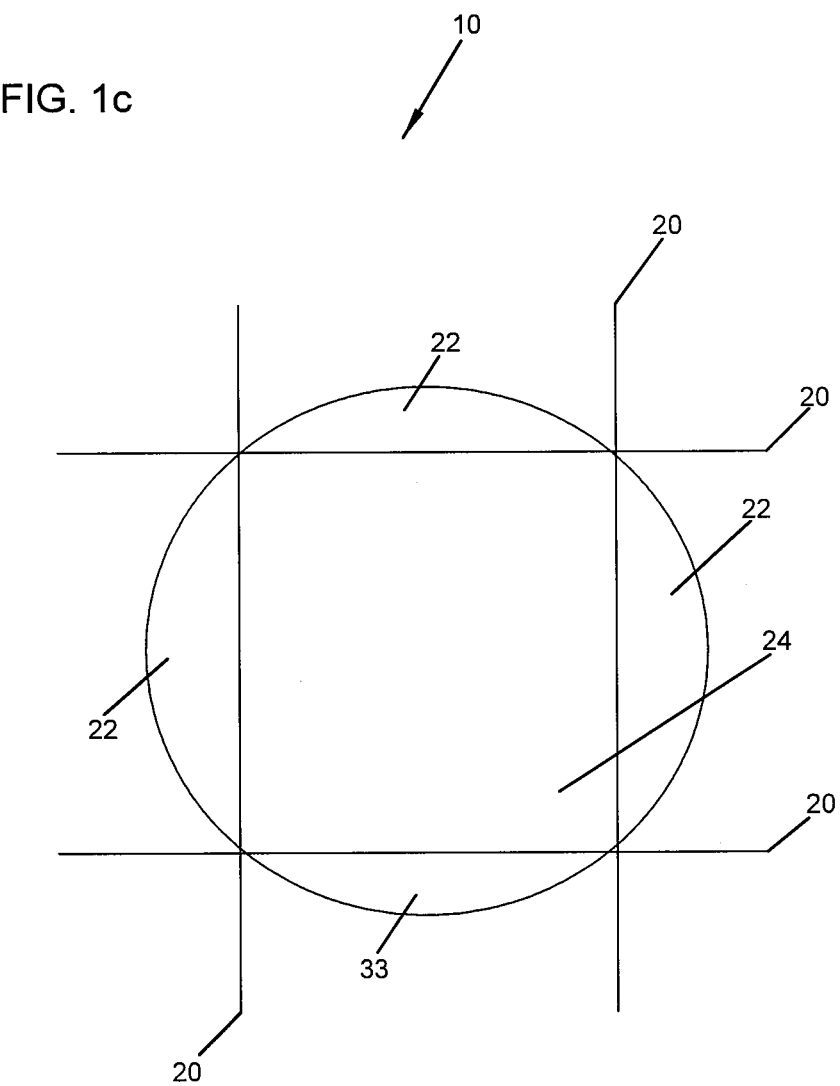
FIG. 1c illustrates a cross-section of a long bone having portions of the periosteal surfaces removed, in accordance with one embodiment.

The manner of milling or separating the layers of the cortical bone may be varied. For example, the bone may be lathed to remove sequential layers. Alternatively, the periosteal layer may be removed by cutting along cut lines 20, as shown in FIG. 1c. The cut lines 20 thus produce segments 22 of bone primarily derived from the periosteal layer. The middle layer and endosteal layer may be separately processed together as a monolith 24 or ground, particulated, or other. Thus, in accordance with various embodiments, each of the periosteal layer, the middle layer, and the endosteal layer may be processed and used in an osteocomposition, either separately or in some combination.

The bone may be milled and ground or otherwise processed into particles of an appropriate size before or after demineralization. It is to be understood that "milled" bone, as used herein, may refer to any form of particulated bone, including fibers, particles, chips, etc. Each layer may be processed separately or some layers may be combined, such as the middle layer and the periosteal layer. The particles may be particulate or fibrous. In some embodiments particles from the endosteal layer may have a configuration different from particles of the periosteal layer or of the middle layer. Thus, in some embodiments, endosteal particles may be particulate and small while periosteal particles may be fibrous and large. Each of the endosteal particles, the middle layer particles, and the periosteal particles may be particulate or fibrous, large or small. The configuration of particles from any given layer may be determined based on desired characteristics of the DBM and/or the implant. Thus, for example, periosteal bone, which is generally more osteoinductive than endosteal bone, as described herein, may be configured to enhance such osteoinductivity, such as by milling into fibers. In certain embodiments, the particle size is greater than 75 microns, such as ranging from about 100 to about 3000 microns, or from about 200 to about 2000 microns. After grinding, the bone particles may be sieved to select those particles of a desired size. In certain embodiments, the particles may be sieved though a 50 micron sieve, a 75 micron sieve, or a 100 micron sieve.

Methods provided herein may further comprise separating the endosteal bone, processing it separately, and using it for other applications. In some applications, osteoinductivity of the bone may be less of a factor and, accordingly, it may be beneficial to use bone that is less osteoinductive, such as endosteal bone. Bone that is more osteoinductive, such as periosteal bone, thus may be retained for applications wherein osteoinductivity is desirable. Separating bone into periosteal layer bone, middle layer bone, and/or endosteal layer bone facilitates achieving different osteoinductive potentials that may be customized to the application of the bone.

In forming the bone particles, description is made of milling bone from a periosteal layer, milling bone from a middle layer, and milling bone from an endosteal layer and of separating the bone from the various layers. It is to be understood that such separation includes separating while milling, for example, by milling the outer layer, moving the milled material, milling the middle layer, moving the milled material, and milling the inner layer. Alternatively, such separation may be done by dividing the bone into the outer layer, middle layer, and inner layer and separately milling each layer. Alternatively, the bone may be milled and separated post-milling, for example, by milling each layer at a different particle size and sifting the milled material.

IV. Demineralize the Bone Particles

DBM may be prepared in any suitable manner. In one embodiment, the DBM is prepared through the acid extraction of minerals from bone. It includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues. As noted, in embodiments of bone particles taken from cortical long bones, the osteoinductive potential of the bone particles when demineralized may vary based on the source of the bone particles, whether from the periosteal layer, the middle layer, or the endosteal layer.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one demineralization procedure, the bone is subjected to an acid demineralization step followed by a defatting/disinfecting step. The bone is immersed in acid to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment. Thus, in various embodiments, the DBM may be fully demineralized, partially demineralized, or surface demineralized.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within a given period of time. A suitable concentration range of the defatting solution is from about 60 to about 85 weight percent alcohol, or about 70 weight percent alcohol.

In some embodiments, the demineralized bone may be further treated to effect properties of the bone. For example, the DBM may be treated to disrupt the collagen structure of the DBM. Such treatment may comprise collagenase treatment, heat treatment, mechanical treatment, or other. Reference is made to U.S. Provisional Patent Applications 60/944,408, 60/944,417, and 60/957,614, herein incorporated by reference, for further treatment options.

V. Optional Additives

In accordance with various embodiments, the DBM provided herein may be used with growth factors, extracts, peptide hormones, or other additives to increase the osteoinductive capacity of the DBM or to impart other benefits to the DBM. It will be appreciated that the amount of additive used will vary depending upon the type of additive, the specific activity of the particular additive preparation employed, and the intended use of the composition. The desired amount is readily determinable by the user.

Any of a variety of medically and/or surgically useful optional substances can be incorporated in, or associated with, the osteoinductive factors either before, during, or after preparation of the osteoinductive composition. Thus, for example when demineralized bone particles are used to form the material, one or more of such substances may be introduced into the demineralized bone particles, for example, by soaking or immersing the bone particles in a solution or dispersion of the desired substance(s).

Medically/surgically useful substances that can be readily combined with the DBM include, for example, collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), angiogenic factors, transforming growth factor (TGF-beta), insulin-like growth factor (IGF-1); growth hormones such as somatotropin; bone digestors; antitumor agents; immunosuppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

In one embodiment, a tissue-derived extract may be added to the DBM. U.S. patent application Ser. Nos. 11/555,606 and 11/555,608 discloses such extracts and addition of such extracts to DBM and is incorporated herein by reference. For example, a tissue-derived extract or partially demineralized bone may be added to the demineralized bone matrix. The extract may be derived from any suitable tissue, such as bone, bladder, kidney, brain, skin, or connective tissue. Further, the extract may be derived in any suitable manner. The extract may be allogenic, autogenic, xenogenic, or transgenic. In embodiments wherein the extract is bone-derived, the bone may be cortical, cancellous, or corticocancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells (e.g. cartilage, fibroblasts, endothelial, etc.) besides osteoblasts. Stem cells may be combined with the DBM. Accordingly, the osteoinductive DBM composition may be used to deliver stem cells, which offers the potential to give rise to different types of cells in the bone repair process. In one embodiment, the osteoconductive DBM composition further comprises a cell such as an osteogenic cell or a stem cell. In various embodiments, the additive may comprise radiopaque substances, angiogenesis promoting materials, bioactive agents, osteoinducing agents, or other. Reference is made to U.S. patent application Ser. Nos. 11/555,606 and 11/555,608 for specific discussion of possible additives.

In certain embodiments, the additive is adsorbed to or otherwise associated with the DBM. The additive may be associated with the osteoinductive DBM composition through specific or non-specific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the osteoinductive DBM composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive composition. An additive may be provided within the osteoinductive composition in a sustained release format. For example, the additive may be encapsulated within biodegradable nanospheres, microspheres, etc.

Any suitable method for adding, or dispersing, the additive to the DBM may be used. Generally, the procedures used to formulate or disperse the additive onto the DBM are sensitive to the physical and chemical state of both the additive and the DBM.

VI. Addition of DBM to Carrier

In various embodiments, the DBM provided herein may be combined, with or without additives, with a carrier or excipient to achieve consistency for specific uses. For example, a carrier may be selected to provide the DBM composition in a gel consistency, a putty consistency, a matrix consistency, or other to form an osteoinductive composition. The osteoinductive composition may be configured to be moldable, extrudable, or substantially solid. The osteoinductive composition may be configured to substantially retain its shape in water for a period of time. The osteoinductive composition may form an osteoimplant useful in clinical applications. Suitable carriers may include surface demineralized bone; mineralized bone; nondemineralized cancellous scaffolds; demineralized cancellous scaffolds; cancellous chips; particulate, demineralized, guanidine extracted, species-specific (allogenic) bone; specially treated particulate, protein extracted, demineralized, xenogenic bone; collagen; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethylchitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions, etc.

Suitable polymeric materials for use as carriers are disclosed in U.S. Patent Publication Nos. 2007/0191963, 2006/0216323, and 2005/0251267, U.S. Pat. Nos. 6,696,073, 6,478,825, 6,440,444, and 6,294,187, all herein incorporated by reference in their entireties for all purposes.

The carrier may further comprise a hydrogel such as hyaluronic acid, dextran, pluronic block copolymers of polyethylene oxide and polypropylene, and others. Suitable polyhodroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Reference is made to U.S. Pat. Nos. 5,284,655 and 5,314,476 for other carriers including polyhydroxy carriers, to U.S. Pat. No. 6,884,778 for biocompatible macromers that may be used as carriers, and to U.S. Patent Publication No. 2003/0152548 for cross-linkable monomers that may be used as carriers, all herein incorporated by reference. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Any suitable shape, size, and porosity of carrier may be used. In some embodiments, the carrier may be settable and/or injectable. Such carrier may be, for example, a polymeric cement, a settable calcium phosphate, a settable poly vinyl alcohol, a polyurethane, or a liquid settable polymer. Suitable settable calcium phosphates are disclosed in U.S. Pat. Nos. 5,336,264 and 6,953,594, which are hereby incorporated by reference. Hydrogel carriers may additionally impart improved spatial properties, such as handling and packing properties, to the osteoconductive composition. An injectable carrier may be desirable where the composition is used with a containment device. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

The carrier may comprise a shape-retaining solid made of loosely adhered particulate material, e.g., with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with DBM and, optionally, the osteoinductive factors.

One way to protect small size particles from cellular ingestion and/or to provide a diffusion barrier is to embed them in a monolithic bioabsorbable matrix, and then fragment the particle-containing monolithic matrix into particle sizes greater than 70 microns, for example, greater than 100 microns, or greater than 150 microns in their smallest dimension. Suitable matrices for embedding DBM compositions include biocompatible polymers and setting calcium phosphate cements. Generally the DBM composition/polymer weight ratio will range from about 1:5 to about 1:3. In the case of calcium phosphate, the DBM may be present up to 75% by weight. In one embodiment, DBM is embedded in a resorbable polymer. In a further embodiment, partially demineralized bone particles are embedded in one of the setting calcium phosphates known to the art.

The carrier may comprise a number of materials in combination, some or all of which may be in the form of fibers and/or particles. The carrier may comprise calcium phosphates. Driessens et al. "Calcium phosphate bone cements," Wise, D. L., Ed., *Encyclopedic Handbook of Biomaterials and Bioengineering, Part B, Applications* New York: Marcel Decker; Elliott, *Structure and Chemistry of the Apatites and Other Calcium Phosphates* Elsevier, Amsterdam, 1994, each of which is incorporated by reference. Calcium phosphate matrices include, but are not limited to, dicalcium phosphate dihydrate, monetite, tricalcium phospate, tetracalcium phosphate, hydroxyapatite, nanocrystalline hydroxyapatite, poorly crystalline hydroxyapatite, substituted hydroxyapatite, and calcium deficient hydroxyapatites.

In one embodiment, the carrier comprises an osteoinductive material such as a mineralized particulated material, osteoinductive growth factors, or partially demineralized bone. The mineralized particulated material may be TCP, hydroxyapatite, mineral recovered from bone, cancellous chips, cortical chips, surface demineralized bone, or other material. The osteoinductive material may be combined with a further carrier such as starch or glycerol. Accordingly, in some embodiments, the partially demineralized bone may act as a carrier for the tissue-derived extract.

The DBM composition may be completely insoluble or may be slowly solubilized after implantation. Following implantation, the composition may resorb or degrade, remaining substantially intact for at least one to seven days, or for two or four weeks or longer and often longer than 60 days. The composition may thus be resorbed prior to one week, two weeks, three weeks, or other, permitting the entry of bone healing cells.

VII. Formation of an Implant

The DBM provided herein may be used to form an osteoinductive implant. The osteoimplant resulting from the DBM, additive, and/or carrier may be flowable, have a putty consistency, may be shaped or molded, and/or may be deformable. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, the implant may retain coherence in fluids.

Accordingly, the osteoinductive DBM composition may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized according to the invention, which may be shaped as a sheet, and processes for fabricating shaped materials from demineralized bone particles is disclosed in U.S. Pat. Nos. 5,507,813 and 6,436,138, respectively, the contents of which are herein incorporated by reference. Suitable sheets include those sold under the trade name Grafton® DBM Flex, which must be wetted/hydrated prior to use to be useful for implantation. Such sheets have recently been reported as effective in seeding human bone marrow stromal cells (BMSCs), which may be useful in the repair of large bone defects. Kasten et al., "Comparison of Human Bone Marrow Stromal Cells Seeded on Calcium-Deficient Hydroxyapatite, Betatricalcium Phosphate and Demineralized Bone Matrix," *Biomaterials*, 24(15):2593-603, 2003. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

In some embodiments, the osteoinductive DBM composition may be placed in a containment device such as a porous mesh to provide a delivery system. In various embodiments, the device may comprise a polymer (such as polyalkylenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), L-co-G, etc.),other bioabsorbable polymer such as Dacron or other known surgical plastics, a natural biologically derived material such as collagen, a ceramic (with bone-growth enhancers, hydroxyapatite, etc.), PEEK (polyether-etherketone), dessicated biodegradable material, metal, composite materials, a biocompatible textile (e.g., cotton, silk, linen), or other. In one embodiment, the containment device is formed as a long bag-like device and may be used with minimally invasive techniques.

VIII. Formulation of DBM Containing Compositions

The osteoinductive DBM composition, the carrier, or the osteoimplant may be formulated for a particular use. The formulation may be used to alter the physical, biological, or chemical properties of the carrier. A physician would readily be able to determine the formulation needed for a particular application, taking into account such factors as the type of injury, the site of injury, the patient's health, and the risk of infection. In various embodiments, the osteoinductive composition may comprise, for example less than approximately 0.5% water, less than approximately 1% water, or less than approximately 5% water.

Osteoinductive DBM compositions, carriers, or osteoimplants therefore may be prepared to have selected resorption/loss of osteoinductivity rates, or even to have different rates in different portions of an implant. For example, the formulation process may include the selection of partially demineralized particles of a particular size or composition, combined with the selection of a particular stabilizing agent or agents, and the amounts of such agents.

Physical properties such as deformability and viscosity of the carrier may also be chosen depending on the particular clinical application. The DBM provided herein may be mixed with partially demineralized bone and/or other materials and factors to improve other characteristics of the implant. For example, the DBM may be mixed with other agents to improve wound healing. These agents may include drugs, proteins, peptides, polynucleotides, solvents, chemical compounds, and biological molecules.

Further, the DBM composition may be formulated to be settable and/or injectable. Thus, for example, the composition may be injectable through a 10-gauge, a 12-gauge, or an 18-gauge needle.

Accordingly, in some embodiments the DBM composition may be rubbery, rubbery with chunks, stiff (as freeze-dried), stiff with chunks, putty, paste, flowable, or injectable. The term "flowable" in this context applies to compositions whose consistencies range from those which can be described as shape-sustaining but readily deformable, e.g., those which behave like putty, to those which are runny. Specific forms of flowable bone powder compositions include cakes, pastes, creams and fillers. Reference is made to U.S. Pat. No. 5,290, 558, herein incorporated by reference in its entirety, for discussion of flowable materials.

Also, as previously discussed, the osteoinductive DBM composition may also be formed into various shapes and configurations, including rods, strings, sheets, weaves, solids, cones, discs, fibers, and wedges. Such shapes may result from a monolithic bone piece or an aggregate of bone particles. In certain embodiments, the shape and size of the DBM affect the time course of osteoinductivity. For example, in a cone or wedge shape, the tapered end will result in osteoinductivity shortly after implantation of the osteoimplant, whereas the thicker end will lead to osteoinductivity later in the healing process (hours to days to weeks later). In certain embodiments, DBM osteoimplants may include an aggregate of bone particles, the particles have a length of greater than 2 mm, greater than 1.5 mm, greater than 1 mm, greater than 500 microns, or greater than 200 microns across its widest dimension. Also, larger particle size will induce bone formation over a longer time course than smaller particles. Particles of different characteristics (e.g., composition, size, shape) may be used in the formation of these different shapes and configurations. For example, the DBM implant may include a sheet of partially demineralized bone, with a layer of long half-life particles alternated between layers of shorter half-life particles. See U.S. Pat. No. 5,899,939, herein incorporated by reference, for suitable examples. In a weave, strands composed of short half-life particles may be woven together with strands of longer half-lives.

In the process of preparing the DBM osteoimplant, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing DBM such as defatting, sonication, and lyophilization may also be used in preparing a DBM carrier. Since the biological activity of demineralized bone is known to be detrimentally affected by most terminal sterilization processes, care must be taken when sterilizing the inventive compositions.

IX. EXAMPLES

Example 1

A section of human femur was milled radially to isolate the radial layers of the diaphyseal bone. After removing the cancellous bone from the marrow cavity, the cortical bone was milled at three depths to obtain samples from the three layers shown in FIG. 1b. Briefly, fibers from the periosteal layer (experimental layer 1) were milled from a depth of approximately about 1.5 mm in thickness and saved. A layer of fibers underneath was then milled and discarded. Next, fibers from the middle of the cortical bone (experimental layer 2) were milled from a depth of about 1.5 mm in thickness and saved. A layer of fibers internal was then milled and discarded. Fibers from the endosteal layer (experimental layer 3) were then milled for a depth of about 1.5 mm. To avoid harvesting any residual cancellous bone, the inner most regions was not milled. After collecting the desired experimental layers, the mineralized fibers were demineralized. The DBM fibers were then implanted in athymic rats and the resulting nodules were explanted after 28 days. The implants comprised 6 outer/periosteal layer implants, 6 middle layer implants, and 6 inner/endosteal implants. Nodules of bone growth surrounding the implants were analyzed by x-ray, micro-CT and semi-quantitatively via histological analysis. The non-collagenous proteins in the DBM fibers were extracted and quantitatively analyzed using an Enzyme-Linked ImmunoSorbent Assay (ELISA).

Figure 2:
FIG. 2 illustrates a collage of X-ray micrographs showing the mineralization of fibers collected from each layer of the cortical bone illustrated in FIG. 1 in athymic rats.

FIG. 2 illustrates the results of the radial specific osteoinduction for the x-ray analysis. FIG. 2 specifically illustrates osteoinduction in athymic rats. Nodules originating from the periosteal layer or outer cortical layer (experimental layer 1) are shown in the left-hand column. Nodules originating from the middle layer are shown in the middle column, and nodules originating from the endosteal layer (experimental layer 3) are shown in the right-hand column. As shown, the nodules from the outer cortical layer are larger, more regular in shape and have a denser appearance than do nodules derived from fibers in the other experimental layers.

Figure 3:
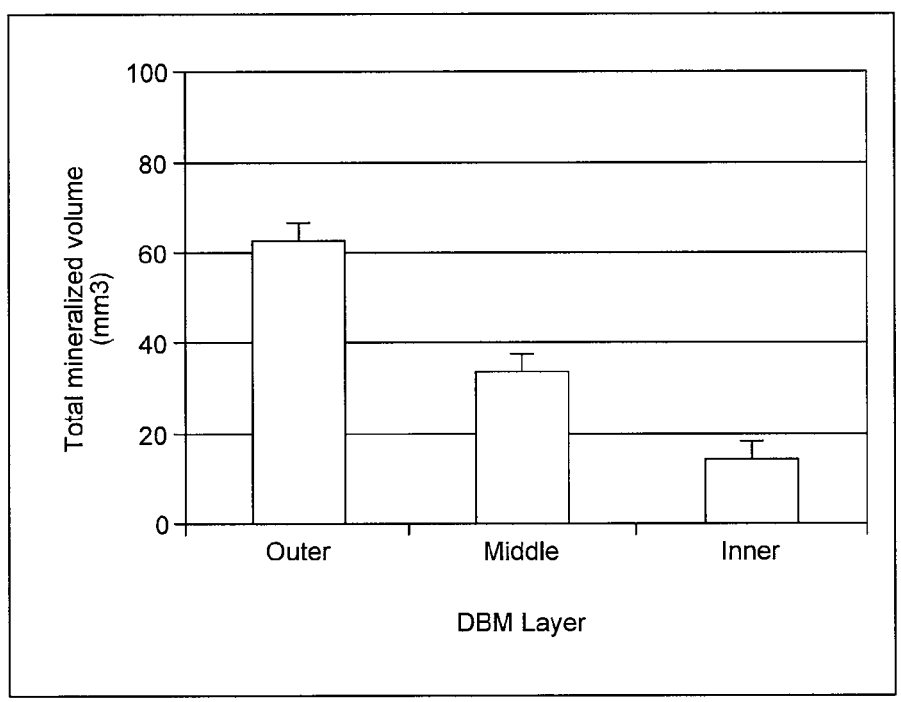
FIG. 3 illustrates a histogram comparing the total bone mineral volume induced by each preparation in heterotopic sites.
Figure 4:
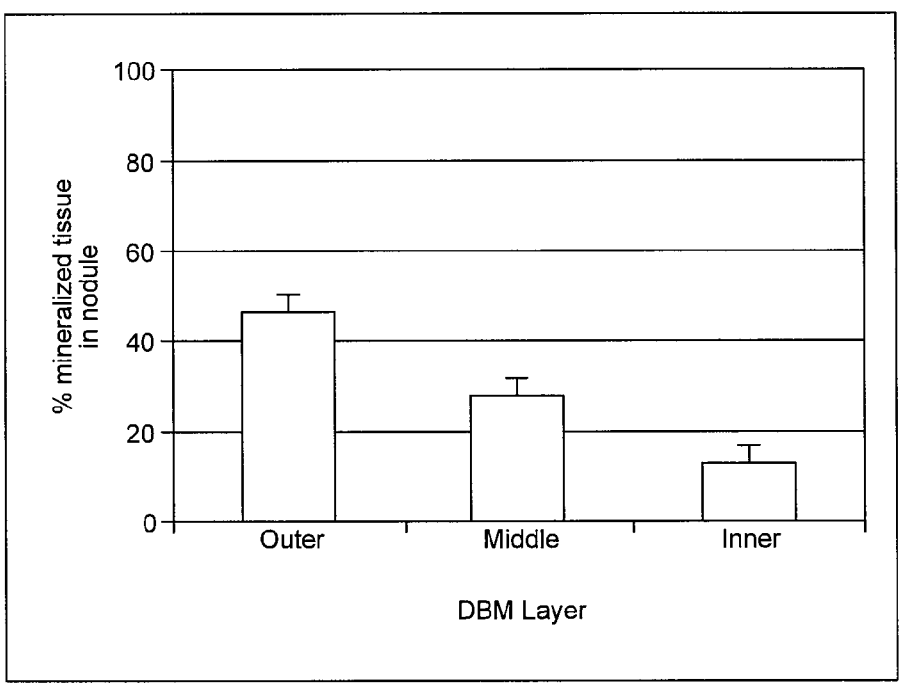
FIG. 4 illustrates a histogram comparing the percentage of total bone mineral volume to total nodule volume by each preparation in heterotopic sites.

FIGS. 3 and 4 illustrate the results of the Micro-CT analysis of the experimental layers. Specifically, FIG. 3 illustrates total bone mineral volume (mm$^3$) for nodules induced by each preparation in heterotopic sites. As illustrated in the graph, experimental layer 1 shows a greater area of bone formation than either of experimental layers 2 or 3, with the middle layer (experimental layer 2) showing greater osteoinduction than the inner/endosteal layer (experimental layer 3).

FIG. 4 compares the percent of new bone in the module from the three cortical bone layers investigated. Thus, FIG. 4 illustrates a histogram comparing the percentage of total bone mineral volume to total nodule volume by each preparation in heterotopic sites. This figure confirms the results of FIG. 2, showing that the outer/periosteal layer (experimental layer 1), has a greater increase in bone formation compared to the middle and inner/endosteal layers with the middle layer showing a greater percentage increase than the inner/endosteal layer.

Figures 5, 6:
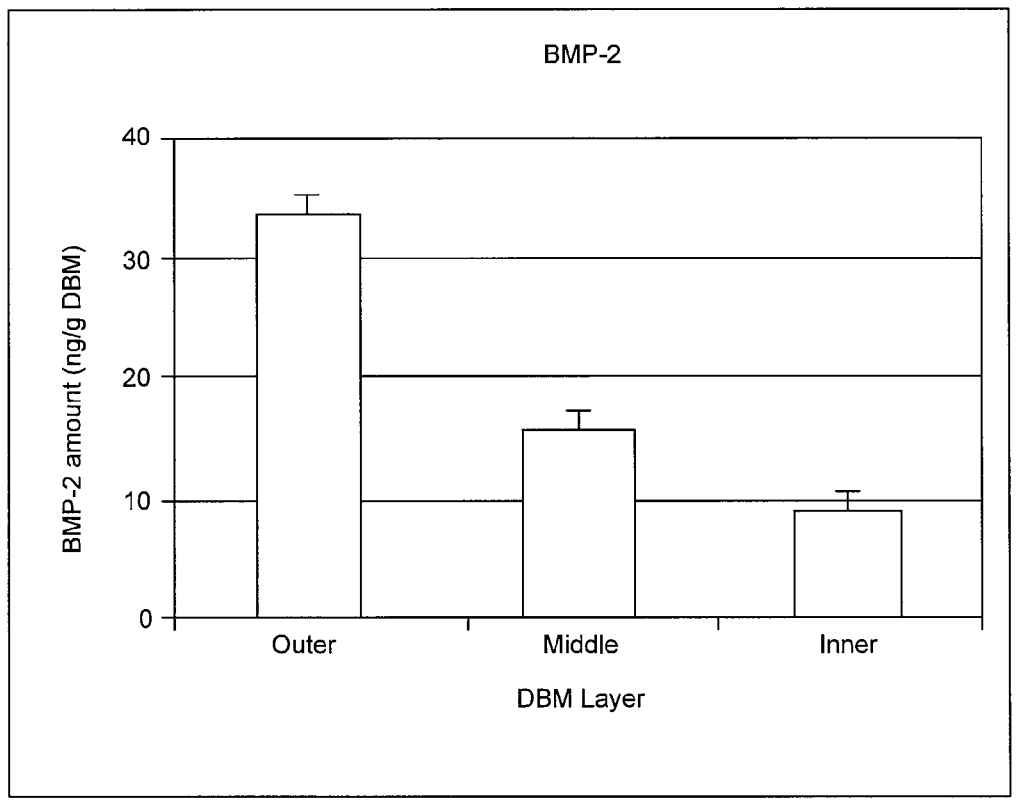
FIG. 5 illustrates a table showing the results of a histological evaluation for each preparation.
FIG. 6 illustrates a histogram comparing the amount of an osteoinductive factor BMP-2 in each preparation.

Results of the histological evaluation of the osteoinductive potential of three bone preparations are shown in FIG. 5. FIG. 5 indicates that the outer/periosteal layer showed greater bone formation than did the middle layer and that the middle layer showed greater induction than the inner/endosteal layer. Specifically, FIG. 5 illustrates a mean osteoinductivity score of 3.17 for the outer/periosteal layer, 2.5 for the middle layer, and 1.83 for the inner/endosteal layer. FIG. 5 thus illustrates the statistical significance of the difference in the osteoinductive (OI) activity of DBM derived from various layers of bone. The histological results are in agreement with the micro-CT and x-ray results in terms of osteoinductive capacity in vivo.

FIG. 6 is a graph showing the amount of BMP-2, an osteoinductive factor, in DBM fibers obtained from three bone preparations, including an outer/periosteal layer preparation, a middle layer preparation, and an inner/endosteal layer preparation. As shown in the graph, the amount of BMP-2 is greater in DBM fibers made from the outer/periosteal layer of the cortical bone than in DBM fibers made from the middle layer. The amount of BMP-2 is greater in DBM fibers made from the middle layer than in DBM fibers made from inner/endosteal layer. The results of BMP-2 amount in three different bone preparations are in agreement with the osteoinductive capacity demonstrated in vivo in athymic rats.

Example 2

A 60 g quantity of demineralized bone particles is prepared from bone from the outer third of a long bone. A 40 g quantity of demineralized bone particles are prepared from bone from the inner two thirds of a long bone. These two quantities are evenly mixed, and then distributed evenly in a glycerol carrier.

Example 3

A 50 g quantity of demineralized bone particles is prepared from bone from the outer two thirds of a long bone. These are distributed in a glycerol carrier.

Example 4

A 60 g quantity of demineralized bone fibers are prepared from bone from the outer third of a long bone. A 40 g quantity of demineralized bone particles are prepared from bone from the inner two thirds of a long bone. These bone particles and bone fibers are mixed and distributed in a glycerol carrier.

Example 5

A 70 g quantity of demineralized bone fibers are prepared from bone from the outer 20% of a long bone. This material is distributed in a glycerol carrier.

Example 6

A 50 g quantity of demineralized bone particles is prepared from bone from the outer 40% of a long bone. A 30 g quantity of demineralized bone fibers is prepared from bone from the inner 60% of a long bone. The demineralized bone fibers are pressed. The bone particles and bone fibers are mixed, and then distributed in a glycerol carrier.

Example 7

An 80 g quantity of demineralized bone fibers are prepared from bone from the outer third of a long bone. The demineralized bone fibers are pressed. A 40 g quantity of surface demineralized bone particles are prepared from bone from the inner two thirds of a long bone. These bone particles and bone fibers are mixed and distributed in a glycerol carrier.

Example 7

An 80 g quantity of demineralized bone fibers and demineralized bone particles are prepared from bone from the outer 40% of a long bone. A 50 g quantity of surface demineralized bone chips are prepared from bone from the inner 60% of a long bone. These bone particles, bone fibers, and bone chips are mixed and distributed in a glycerol carrier.

Example 7

An 60 g quantity of demineralized bone chips are prepared from bone from the outer third of a long bone. A 30 g quantity of demineralized bone particles are prepared from bone from the inner two thirds of a long bone. These bone chips and particles are mixed and distributed in a glycerol carrier.

X. Conclusion

Data contained herein discloses the different osteoinductive potential of demineralized bone matrix arising from different layers of cortical bone. DBM derived from the outer/periosteal layer of bone has a greater osteoinductive capacity than DBM derived from the middle layer of bone which, in turn, has a greater osteoinductive capacity than DBM derived from the inner/endosteal layer of the bone.

In some embodiments, a DBM composition comprising DBM derived from the outer/periosteal of bone, and substantially free of bone derived from the middle or inner/endosteal layers, is provided. A DBM composition produced from bone from the periosteal layer has a BMP-2, without addition of exogenous growth factor or DBM extract, content exceeding a DBM composition from bone derived from other layers or from a mixture of layers. This also applies to content of BMP-3, BMP-4, BMP-5, BMP-6, BMP-7, and TGF-beta.

While the DBM compositions provided herein derived from the outer/periosteal layer, or substantially free of bone derived from the inner/endosteal layer, can be used without further additives, it is understood that the DBM may be carriers, excipients, extracts, and/or growth factors. Further, the DBM compositions according to the invention can be included in a carrier device or prosthesis to form an implant that provides a platform for osteogenesis and resulting in de novo bone growth.

Although the invention has been described with reference to specific embodiments, persons skilled in the art will recognize that changes may be made in form and detail without departing from the spirit and scope of the invention.

What is claimed is:

1. A demineralized bone matrix composition comprising
   cortical bone milled from a periosteal layer; and
   cortical bone milled from a middle layer and an endosteal layer,
   wherein the cortical bone milled from the periosteal layer, the middle layer and the endosteal layer is separated and demineralized such that, upon recombination of the milled cortical bone from the periosteal layer, the middle layer and the endosteal layer, the composition includes a disproportionately greater percentage of cortical bone derived from the periosteal layer as compared to cortical bone derived from the middle layer and the endosteal layer.

2. The demineralized bone matrix composition of claim 1, comprising cortical bone derived from a long bone.

3. The demineralized bone matrix composition of claim 1, wherein the demineralized bone matrix composition has an osteoinductive capacity that is greater than the osteoinductive capacity of a demineralized bone matrix having a lesser percentage of cortical bone derived from the periosteal layer.

4. The demineralized bone matrix composition of claim 1, wherein the demineralized bone matrix composition has an osteoinductive capacity that is greater than the osteoinductive capacity of a demineralized bone matrix having a lesser percentage of cortical bone derived from the endosteal layer.

5. The demineralized bone matrix composition of claim 1, wherein the demineralized bone matrix composition has an average growth factor content exceeding that of a demineralized bone matrix derived from endosteal layer.

6. The demineralized bone matrix composition of claim 1, further including an excipient.

7. The demineralized bone matrix composition of claim 1, further including a carrier.

8. The demineralized bone matrix composition of claim 7, wherein the carrier is selected from the group consisting of: a polyol, a polysaccharide, a hydrogel, a polymer and combinations thereof.

9. The demineralized bone matrix composition of claim 1, further including a growth factor.

10. An allograft composition comprising demineralized bone matrix wherein the demineralized bone matrix is comprised of
    cortical bone milled from a periosteal layer; and
    cortical bone milled from a middle layer and an endosteal layer,
    wherein the cortical bone milled from the periosteal layer, the middle layer and the endosteal layer is separated and demineralized such that, upon recombination of the milled cortical bone from the periosteal layer, the middle layer and the endosteal layer, the composition includes a disproportionately greater percentage of cortical bone derived from the periosteal layer as compared to cortical bone derived from the middle layer and the endosteal layer.

11. The allograft composition of claim 10, wherein the demineralized bone matrix is substantially free of bone derived from an endosteal layer.

12. A demineralized bone matrix composition comprising
    cortical bone milled from a periosteal layer; and
    cortical bone milled from a middle layer and an endosteal layer, wherein the cortical bone milled from the periosteal layer, the middle layer and the endosteal layer is separated and demineralized such that, upon recombination of the milled cortical bone from the periosteal layer, the middle layer and the endosteal layer, the composition includes a disproportionately greater percentage of demineralized bone derived from the periosteal layer as compared to cortical bone derived from the middle layer and the endosteal layer wherein the demineralized bone matrix composition has no exogenous growth factor or demineralized bone matrix (DBM) extract, and wherein the demineralized bone matrix composition has an osteoinductive factor content greater than demineralized bone matrix comprising bone derived from the non-periosteal layer as compared to demineralized bone matrix comprising bone derived from the periosteal layer.

13. The demineralized bone matrix of claim 12, further comprising adding the demineralized cortical bone matrix to a carrier.

14. The demineralized bone matrix of claim 12, further comprising adding the demineralized cortical bone matrix to an excipient.

15. The demineralized bone matrix of claim 12, further comprising adding a growth factor to the demineralized bone.

16. The demineralized bone matrix of claim 12, further comprising adding an extract to the demineralized bone.

17. The demineralized bone matrix of claim 12, further comprising providing a containment device and providing the demineralized cortical bone in the containment device.

18. A composition comprising demineralized cortical bone wherein the composition comprises cortical bone milled from a periosteal layer; and cortical bone milled from a middle layer and an endosteal layer, wherein the cortical bone milled from the periosteal layer, the middle layer and the endosteal layer is separated and demineralized such that, upon recombination of the milled cortical bone from the periosteal layer, the middle layer and the endosteal layer, the composition includes a higher osteoinductive activity than cortical demineralized bone prepared from aggregate long bones of the same donor, wherein the increase in osteoinductive activity is not attributed to addition of growth factors or treatment with enzymes, but is a consequence of selective demineralization of a specific region of a long bone or a specific type of long bone.

* * * * *